US008664174B2

(12) United States Patent
Braeckman et al.

(10) Patent No.: US 8,664,174 B2
(45) Date of Patent: Mar. 4, 2014

(54) COMPOSITION COMPRISING MICROCAPSULES

(75) Inventors: Karl Ghislain Braeckman, Gerpinnes (BE); Karel Jozef Maria Depoot, Anzegem-Vichte (BE); Tim Roger Michel Van Pachtenbeke, Puurs (BE); Johan Smets, Lubbeek (BE)

(73) Assignee: The Procter & Gamble Company, Cincinnati, OH (US)

( * ) Notice: Subject to any disclaimer, the term of this patent is extended or adjusted under 35 U.S.C. 154(b) by 570 days.

(21) Appl. No.: 12/569,026

(22) Filed: Sep. 29, 2009

(65) Prior Publication Data

US 2010/0080831 A1 Apr. 1, 2010

(30) Foreign Application Priority Data

Sep. 30, 2008 (EP) .................................... 08165469

(51) Int. Cl.
*C11D 17/04* (2006.01)
*C11D 3/50* (2006.01)
*C11D 17/00* (2006.01)
*A61K 8/02* (2006.01)

(52) U.S. Cl.
USPC ........... 510/296; 510/221; 510/276; 510/337; 510/405; 510/418; 510/475; 510/523; 512/4; 424/401; 424/419

(58) Field of Classification Search
USPC ......... 510/276, 337, 405, 418, 475, 523, 296, 510/221; 512/4; 424/401, 419
See application file for complete search history.

(56) References Cited

U.S. PATENT DOCUMENTS 2,220,099 A 11/1940 Guenther et al.
2,477,383 A 7/1949 Lewis
3,308,067 A 3/1967 Diehl
3,341,466 A 9/1967 Brynko et al.
3,516,941 A 6/1970 Matson
3,577,515 A 5/1971 Vandegaer
3,664,961 A 5/1972 Norris
3,723,322 A 3/1973 Diehl
3,835,163 A 9/1974 Rapko
3,919,678 A 11/1975 Penfold
3,923,679 A 12/1975 Rapko
4,102,903 A 7/1978 Crutchfield et al.
4,120,874 A 10/1978 Crutchfield et al.
4,144,226 A 3/1979 Crutchfield et al.
4,145,184 A * 3/1979 Brain et al. ........................ 8/137
4,158,635 A 6/1979 Crutchfield et al.
4,222,905 A 9/1980 Cockrell, Jr.
4,239,659 A 12/1980 Murphy
5,066,419 A 11/1991 Walley et al.
5,154,842 A 10/1992 Walley et al.
5,576,282 A 11/1996 Miracle et al.
5,646,101 A 7/1997 MacBeath
5,686,014 A 11/1997 Baillely et al.
5,695,679 A 12/1997 Christie et al.
5,698,504 A 12/1997 Christie et al.
5,705,464 A 1/1998 Scheper et al.
5,710,115 A 1/1998 Patel et al.
6,020,066 A 2/2000 Weisser et al.
6,306,812 B1 10/2001 Perkins et al.
6,326,348 B1 12/2001 Vinson et al.
6,544,926 B1 4/2003 Bodmer et al.
6,592,990 B2 7/2003 Schwantes
6,869,923 B1 3/2005 Cunningham et al.
2003/0125222 A1 7/2003 Jahns et al.
2007/0082829 A1 4/2007 Smets et al.
2007/0138671 A1 6/2007 Anastasiou et al.
2007/0191256 A1 8/2007 Fossum et al.
2007/0202063 A1 8/2007 Dihora et al.
2008/0014393 A1* 1/2008 Denome et al. .............. 428/35.7
2008/0118568 A1* 5/2008 Smets et al. .................. 424/489
2008/0131695 A1* 6/2008 Aouad et al. .................. 428/338
2008/0305982 A1* 12/2008 Smets et al. .................. 510/441
2010/0086575 A1* 4/2010 Dihora et al. ................. 424/401
2010/0261629 A1* 10/2010 Smets et al. .................. 510/107
2011/0086788 A1* 4/2011 Smets et al. .................. 510/105
2012/0052027 A9* 3/2012 Dihora et al. ................... 424/59

FOREIGN PATENT DOCUMENTS

EP 0 385 534 B1 4/1994
GB 0 751 600 A 6/1956
WO WO 03/101600 A1 12/2003

OTHER PUBLICATIONS

International Search Report—8 pages, PCT/US2009/057789 dated Jan. 14, 2010.

* cited by examiner

*Primary Examiner* — Lorna M Douyon
(74) *Attorney, Agent, or Firm* — Melissa G. Krasovec; Steven W. Miller

(57) ABSTRACT

A liquid composition having a microcapsule, the microcapsule having an aldehyde-containing resin, and one or more formaldehyde scavenger which reacts with formaldehyde to achieve more than about 60% reaction completeness in about 15 minutes time at pH 8 and at about 21° C. A liquid composition having a microcapsule, the microcapsule having an aldehyde-containing resin, one or more sulfur-based formaldehyde scavenger and optionally a non-sulfur-based formaldehyde scavenger.

7 Claims, 1 Drawing Sheet

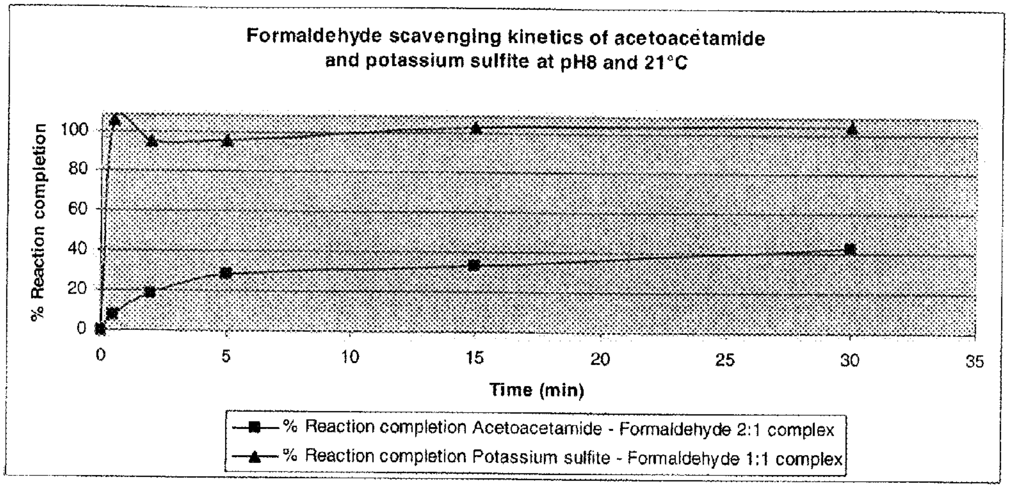
Formaldehyde scavenging kinetics of acetoacetamide
and potassium sulfite at pH8 and 21°C
% Reaction completion
100
80
60
40
20
0
0
5
10
15
20
25
30
35
Time (min)
% Reaction completion Acetoacetamide - Formaldehyde 2:1 complex
% Reaction completion Potassium sulfite - Formaldehyde 1:1 complex

COMPOSITION COMPRISING MICROCAPSULES

FIELD OF THE INVENTION

The present invention relates to a liquid composition comprising microcapsules, said microcapsules comprising a formaldehyde-containing resin, and a formaldehyde scavenger with fast reaction kinetics. More preferably the scavenger is a sulfur-based formaldehyde scavenger. The composition preferably additionally comprises at least one further formaldehyde scavenger present in the premix slurry of the microcapsule, which is added to a final product liquid composition. Said further formaldehyde scavenger added via the slurry, may be sulfur-based, but is preferably non-sulfur based.

BACKGROUND TO THE INVENTION

Benefit agents, such as perfumes, silicones, waxes, flavors, vitamins and fabric softening agents, are expensive and generally less cost effective when employed at high levels in personal care compositions, cleaning compositions, and fabric care compositions. As a result, there is a desire to maximize the effectiveness of such benefit agents. One method of achieving such objective is to improve the delivery efficiency and active lifetime of the benefit agent. This can be achieved by providing the benefit agent as a component of a microcapsule.

Microcapsules are made either by supporting the benefit agent on a water-insoluble porous carrier or by encapsulating the benefit agent in a water-insoluble shell. In the latter category microencapsulates are made by precipitation and deposition of polymers at the interface, such as in coacervates, for example as disclosed in GB-A-O 751 600, U.S. Pat. No. 3,341,466 and EP-A-0 385 534, or other polymerisation routes such as interfacial condensation U.S. Pat. No. 3,577,515, US-A-2003/0125222, U.S. Pat. No. 6,020,066, WO2003/101606, U.S. Pat. No. 5,066,419. A particularly useful means of encapsulation is using the melamine/urea-formaldehyde condensation reaction as described in U.S. Pat. No. 3,516,941, U.S. Pat. No. 5,066,419 and U.S. Pat. No. 5,154,842. Such capsules are made by first emulsifying a benefit agent in small droplets in a pre-condensate medium obtained by the reaction of melamine/urea and formaldehyde and then allowing the polymerisation reaction to proceed along with precipitation at the oil-water interface. The encapsulates ranging in size from a few micrometer to a millimeter are then obtained in a suspension form in an aqueous medium.

Microcapsules provide several benefits. They have the benefit of protecting the benefit agent from physical or chemical reactions with incompatible ingredients in the composition, volatilization or evaporation. Microcapsules have the further advantage in that they can deliver the benefit agent to the substrate and can be designed to rupture under desired conditions, such as when a fabric becomes dry. Microcapsules can be particularly effective in the delivery and preservation of perfumes. Perfumes can be delivered to and retained within the fabric by a microcapsule that only ruptures, and therefore releases the perfume, when the fabric is dry.

Preferred microcapsules have a core-in-shell architecture and comprise a shell of formaldehyde-containing resin. The Applicants have found, however, that when such microcapsules are formulated into a composition, regardless of the content of the core of the microcapsule, the composition containing said microcapsule becomes discoloured. Particularly problematic is a blue product discolouring to green. This is particularly problematic when the product is packaged in a transparent or translucent container. Discoloration appears to be dependent on microcapsule level and storage temperature. Higher storage temperature and/or higher concentration of microcapsule results in a product that discolours faster and with more colour depth.

SUMMARY OF THE INVENTION

According to the present invention there is provided a liquid composition comprising a microcapsule, comprising an aldehyde-containing resin, and one or more formaldehyde scavenger which reacts with formaldehyde to achieve more then 60% reaction completeness in 15 minutes time at pH 8 and at 21° C.

According to the present invention there is further provided a liquid composition comprising a microcapsule comprising an aldehyde-containing resin, one or more sulfur-based formaldehyde scavenger and optionally one or more non-sulfur based formaldehyde scavenger.

According to the present invention there is also provided a process of preparing the composition comprising the steps of:
i) preparing a slurry of microcapsules comprising an aldehyde-containing resin and optionally one or more formaldehyde scavenger;
ii) adding said slurry to a composition comprising one or more sulfur-based formaldehyde scavenger.

BRIEF DESCRIPTION OF THE DRAWINGS

The present disclosure may be more readily understood with reference to the appended drawing figures where:

FIG. 1 is a plot showing formaldehyde scavenger kinetics.

DETAILED DESCRIPTION OF THE INVENTION

The liquid compositions of the present invention are preferably suitable for use as laundry or hard surface cleaning treatment compositions.

The term liquid is meant to include viscous or fluid liquids with newtonian or non-Newtonian rheology and gels. Said composition may be packaged in a container or as an encapsulated unitized dose. The latter form is described in more detail below. Liquid compositions may be aqueous or non-aqueous. Where the composition is aqueous it may comprise from 20% to 90% water, more preferably from 20% to 80% water and most preferably from 25% to 65% water. Non-aqueous compositions comprise less than 20% water, preferably less than 15%, most preferably less than 10% water. Compositions used in unitized dose products comprising a liquid composition enveloped within a water-soluble film are often described to be non-aqueous. Compositions according to the present invention for this use preferably comprise from 2% to 15% water, more preferably from 2% to 10% water and most preferably from 4% to 10% water.

The compositions of the present invention preferably have viscosity from 1 to 10000 centipoises (1-10000 mPa*s), more preferably from 100 to 7000 centipoises (100-7000 mPa*s), and most preferably from 200 to 1500 centipoises (200-1500 mPa*s) at 20 $s^{-1}$ and 21° C. Viscosity can be determined by conventional methods. Viscosity according to the present invention however is measured using an AR 550 rheometer from TA instruments using a plate steel spindle at 40 mm diameter and a gap size of 500 μm.

Microcapsule

The microcapsule of the present invention comprises an aldehyde-containing resin. More preferably the microcapsule has a core-in-shell structure. More preferably the shell is an aminoplast. Most preferably the microcapsule comprises a formaldehyde-containing shell.

The microcapsule preferably comprises a core material and a shell wall material that at least partially, preferably completely surrounds the core material. Said microcapsule preferably has:

a.) a particle size coefficient of variation of from about 1.5 to about 6.0, from about 2.0 to about 3.5, or even from about 2.5 to about 3.2;

b.) a fracture strength of from about 0.1 psia to about 110 psia, from about 1 to about 50 psia, or even from about 4 to about 16 psia;

c.) a benefit agent retention ratio of from about 2 to about 110, from about 30 to about 90, or even from about 40 to about 70; and d.) an average particle size of from about 1 micron to about 100 microns, from about 5 microns to about 80 microns, or even from about 15 microns to about 50 microns.

(1) Benefit Agent Retention Ratio a.) Add 1 gram of particle to 99 grams of composition that the particle will be employed in.

b.) Age the particle containing composition of a.) above for 2 weeks at 40° C. in a sealed, glass jar.

c.) Recover the particles from b.) above by filtration.

d.) Treat the particles of c.) above with a solvent that will extract all the benefit agent from the particles.

e.) Inject the benefit agent containing solvent from d.) above into a Gas Chromatograph and integrate the peak areas to determine the total quantity of benefit agent extracted from the particle sample.

f.) This quantity is then divided by the quantity that would be present if nothing had leaked out of the microcapsule (e.g. the total quantity of core material that is dosed into the composition via the microcapsules). This value is then multiplied by the ratio of average particle diameter to average particle thickness to obtain a Benefit Agent Retention Ratio.

A detailed analytical procedure to measure the Benefit Agent Retention Ratio is:

ISTD Solution

Weigh out 25 mg dodecane into a weigh boat. Rinse the dodecane into a 1000 mL volumetric flask using ethanol. Add ethanol to volume mark. Stir solution until mixed. This solution is stable for 2 months.

Calibration Standard

Weigh out 75 mg of core material into a 100 mL volumetric flask. Dilute to volume with ISTD solution to from above. This standard solution is stable for 2 months. Mix well. Analyze via GC/FID.

Basic Sample Prep (Prepare Samples in Triplicate)

Weigh 1.000 gram sample of aged composition containing particles into a 100 mL tri-pour beaker. Record weight. Add 4 drops (approximately 0.1 gram) 2-ethyl-1,3-Hexanediol into the tri-pour beaker. Add 50 mL Deionized water to the beaker. Stir for 1 minute. Using a 60 cc syringe, filter through a Millipore Nitrocellulose Filter Membrane (1.2 micron, 25 mm diameter). Rinse through the filter with 10 mL of Hexane. Carefully remove the filter membrane and transfer to a 20 mL scintillation vial (using tweezers). Add 10 mL ISTD solution (as prepared above) to the scintillation vial containing the filter. Cap tightly, mix, and heat vial at 60° C. for 30 min. Cool to room temperature. Remove 1 mL and filter through a 0.45-micron PTFE syringe filter into GC vial. Several PTFE filters may be required to filter a 1 mL sample aliquot. Analyze via GC/FID.

GG/FID Analysis Method:

Column—30 m×0.25 mm id, 1-um DB-1 phase. GC—6890 GC equipped with EPC control and constant flow capability. Method—50° C., 1 min. hold, temperature ramp of 4° C./min. to 300° C., and hold for 10 min.

Injector—1 uL splitless injection at 240° C.

GC/FID Analysis Method—Microbore Column Method:

Column—20 m×0.1 mm id, 0.1 μm DB-5. GC—6890 GC equipped with EPC control and constant flow capability (constant flow 0.4 mL/min). Method—50° C., no hold, temperature ramp of 16° C./min to 275° C., and hold for 3 min. Injector—1 μL split injection (80:1 split) at 250° C.

Calculations:

$$\%\ \text{Total Perfume} = \frac{A_{IS} \times W_{per\text{-}std} \times A_{per\text{-}sam}}{A_{per\text{-}std} \times A_{is\text{-}sam} \times W_{sam}} \times 100\%$$

where $A_{is}$=Area of internal standard in the core material calibration standard; $W_{per\text{-}std}$=weight of core material in the calibration sample; $A_{per\text{-}sam}$=Area of core material peaks in the composition containing particle sample; $A_{per\text{-}std}$=Area of core material peaks in the calibration sample; $A_{is\text{-}sam}$=Area of internal standard in composition containing particle sample; $W_{sam}$=Weight of the composition containing particle sample $$\text{Retention\_Ratio} = \left(\frac{\text{Total\_Perfume}}{\text{Perfume\_Dosed\_Into\_Product\_Via\_Microcapsules}}\right)\left(\frac{\mu}{T}\right)$$

where

μ is the average particle diameter, from Test Method 1 and T is the average particle thickness as calculated from Test Method 3

(2) Fracture Strength a.) Place 1 gram of particles in 1 liter of distilled deionized (DI) water.

b.) Permit the particles to remain in the DI water for 10 minutes and then recover the particles by filtration.

c.) Determine the average rupture force of the particles by averaging the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the average fracture pressure by dividing the average rupture force (in Newtons) by the average cross-sectional area (as determined by Test Method 1 above) of the spherical particle ($\pi r^2$, where r is the radius of the particle before compression).

d.) Calculate the average fracture strength by using the following equation:

$$\sigma_{fracture\_stress} = \frac{P}{4(d/T)}$$

where

P is the average fracture pressure from a.) above, d is the average diameter of the particle (as determined by Test Method 1 above), T is the average shell thickness of the particle shell as determined by the following equation:

$$T = \frac{r_{capsule}(1-c)\rho_{perfume}}{3[c\rho_{wall} + (1-c)\rho_{perfume}]}$$

where c is the average perfume content in the particle; r is the average particle radius; $\rho_{wall}$ is the average density of the shell as determined by ASTM method B923-02, "Standard Test Method for Metal Powder Skeletal Density by Helium or Nitrogen Pycnometry", ASTM International. $\rho_{perfume}$ is the average density of the perfume as determined by ASTM method D1480-93 (1997) "Standard Test Method for Density and Relative Density (Specific Gravity) of Viscous Materials by Bingham Pycnometer", ASTM International.

In one aspect of the Applicants' invention, said microcapsule may have and/or comprise any combination of the parameters described in the present specification.

Suitable microcapsule wall materials include materials selected from the group consisting of reaction products of one or more amines with one or more formaldehydes, such as urea cross-linked with formaldehyde or gluterformaldehyde, melamine cross-linked with formaldehyde; gelatin-polyphosphate coacervates cross-linked with gluterformaldehyde; and mixtures thereof. In one aspect, the wall material comprises melamine cross-linked with formaldehyde.

Useful core benefit agents include perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. In one aspect, said perfume raw material is selected from the group consisting of alcohols, ketones, formaldehydes, esters, ethers, nitriles alkenes. In one aspect, said perfume may comprise a perfume raw material selected from the group consisting of perfume raw materials having a boiling point (B.P.) lower than about 250° C. and a ClogP lower than about 3, perfume raw materials having a B.P. of greater than about 250° C. and a ClogP of greater than about 3, perfume raw materials having a B.P. of greater than about 250° C. and a ClogP lower than about 3, perfume raw materials having a B.P. lower than about 250° C. and a ClogP greater than about 3 and mixtures thereof. Perfume raw materials having a boiling point B.P. lower than about 250° C. and a ClogP lower than about 3 are known as Quadrant I perfume raw materials, perfume raw materials having a B.P. of greater than about 250° C. and a ClogP of greater than about 3 are known as Quadrant IV perfume raw materials, perfume raw materials having a B.P. of greater than about 250° C. and a ClogP lower than about 3 are known as Quadrant II perfume raw materials, perfume raw materials having a B.P. lower than about 250° C. and a ClogP greater than about 3 are known as a Quadrant III perfume raw materials. In one aspect, said perfume comprises a perfume raw material having B.P. of lower than about 250° C. In one aspect, said perfume comprises a perfume raw material selected from the group consisting of Quadrant I, II, III perfume raw materials and mixtures thereof. In one aspect, said perfume comprises a Quadrant III perfume raw material. Suitable Quadrant I, II, III and IV perfume raw materials are disclosed in U.S. Pat. No. 6,869,923 B1.

Process of Making Microcapsules and Slurry Containing Microcapsules

Microcapsules are commercially available. Processes of making said microcapsules is described in the art. More particular processes for making suitable microcapsules are disclosed in U.S. Pat. No. 6,592,990 B2 and/or U.S. Pat. No. 6,544,926 B1 and the examples disclosed herein.

The slurry of the present invention is the composition resulting from this manufacturing process. Said slurry comprises microcapsules, water and precursor materials for making the microcapsules. The slurry may comprise other minor ingredients, such as an activator for the polymerization process and/or a pH buffer. To the slurry, a formaldehyde scavenger may be added.

Formaldehyde Scavenger

The Applicants have found that compositions comprising formaldehyde-containing microcapsules discolour over time. This phenomenon exists even in the absence of any benefit agent at the core of the microcapsule. The Applicants have further found that there is a preferred selection in the choice of formaldehyde scavenger to achieve the most stable, especially colour stable final composition. In one embodiment of the present invention, the composition comprises one or more sulfur-based formaldehyde scavenger. The liquid composition optionally additionally comprises one or more non-sulfur-based formaldehyde scavenger.

The sulfur-based scavenger may be added to the slurry containing the microcapsules prior to addition to the composition. However, high levels of sulfur-based scavenger in the slurry could result in high levels of sulfur dioxide emission, which would be regarded as a plant safety issue. The sulfur-based formaldehyde scavenger is therefore preferably added directly to the product. The non-sulfur based scavenger, where present, is preferably added to the slurry containing the microcapsules prior to addition to the composition to ensure adequate formaldehyde control in the slurry. The Applicants have found that if a non-sulfur based scavenger is added directly to the detergent composition, even if also added via the slurry, the composition continues to show discolouration, despite the presence of scavenger.

The non-sulfur based formaldehyde scavenger is preferably selected from the group consisting of urea, ethylene urea, lysine, glycine, serine, carnosine, histidine, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, benzotriazol, triazole, indoline, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxformaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, ammonium hydroxide or a mixture thereof. Preferably said non-sulfur-based scavenger is selected from the group consisting of acetoacetamide, ammonium hydroxide and mixtures thereof.

The sulfur-based formaldehyde scavenger is selected from derivatives of sulphate. More particularly it is selected from the group consisting of alkali or alkali earth metal dithionites, pyrosulfites, sulfites, bisulfite, metasulfite, monoalkyl sulphite, dialkyl sulphite, dialkylene sulphite, sulfides, thiosulfates and thiocyanates (e.g. potassium thiocyanate), mercaptans, such as thioglycolic acid, mercaptoethanol, 4-hydroxy-2-mercapto-6-methylpyrimidine, mercaptothiazoline, thiodialkanoic acids, such as thiodipropionic acid, dithiodialkanoic acids, such as 3,3'-dithiodipropionic acid, sulfinates, such as sodium formaldehydesulfoxylate or formamidinosulfinic acid, thiourea or mixtures thereof. Said scavenger activity is preferably pH independent. Preferably said sulfur based scavenger is selected from alkali or alkali earth metal sulfite, bisulfite or mixtures thereof. Most preferably the sulfur-based scavenger is potassium sulfite.

The sulfur-based scavenger according to the present invention is present at a total level, based on total liquid composition weight, of from about 0.001% to about 2.0%, more preferably from about 0.01% to about 0.5%. Where non-sulfur based formaldehyde scavenger is present, it is preferably present in the composition at a total level of about 0.0001% to 1%, more preferably 0.001% to 0.2% based on the liquid composition weight. The ratio of the non-sulfur based scavenger to the sulfur based scavenger, in the liquid composition, is preferably from 0.001:1 to 5:1, more preferably from 0.01:1 to 1:1. The ratio of the sulfur based scavenger to microcapsule wall material is preferably from 0.05:1 to 10:1, more preferably from 0.1:1 to 6:1. The level of microcapsule wall material is a measure of the level of wall material ingredients used in the microcapsule wall material making process, for example described in the Examples.

In one embodiment of the present invention there is provided a liquid composition comprising a microcapsule, comprising an aldehyde-containing resin, and one or more formaldehyde scavenger which reacts with formaldehyde in such way as to achieve more then 60% reaction completeness in 15 minutes time at pH 8 at 21° C. Without being bound by theory, it is believed that the sulfur-containing scavenger prevents product discoloration through fast reaction with formaldehyde present in the product (see graph below). Scavenging reaction kinetics are believed to be affected by a number of factors including; low molecular weight scavengers are more mobile to react with formaldehyde; simple scavenging reaction is faster than complex, multiple stage reactions, water-solubility of the scavenger, as the scavenger must be in the same phase as the formaldehyde. Materials which react with formaldehyde at the same or faster rate also prevent discoloration in the same manner.

Formaldehyde Scavenging Test Method:

The assessment of the scavenging kinetics of a formaldehyde scavenger is performed through quantification of the formed reaction product. The % reaction completion is defined as the measured amount of reaction product divided by the maximum amount of reaction product that can be formed theoretically (assuming that all formaldehyde has been scavenged by the scavenger).

The kinetic experiments are conducted in a commercially available buffer at pH8 (Merck n° 1.09460, based on a boric acid/sodium hydroxyde/hydrogen chloride mix) at 21° C. To this buffer, 0.2 wt % of formaldehyde and 2× the theoretical level of scavenger needed to scavenge all formaldehyde (assuming that all formaldehyde has been scavenged), is added and mixed. For example to define the reaction kinetics of formaldehyde and potassium sulfite, 1 to 1 molar reaction, 2.1 wt % potassium sulfite is added to 0.2 wt % formaldehyde. The yield of the reaction between formaldehyde and scavenger in the liquid mixture is measured directly by mass spectrometry. For the purposes of the experiments herein, the Applicants used a triple-quadruple Mass Spectrometer (API3000 from Sciex Applied Biosystems). The mass spectrometer is tuned to monitor the sulfite/formaldehyde 1/1 reaction product (hydroxymethane sulfonic acid) and the acetoacetamide/formaldehyde 2/1 reaction product (2,4-diacetylglutaramide) over time. Measurements are taken according to the suppliers manual.

FIG. 1 is a plot of the percentage of reaction completion vs. formaldehyde scavenging kinetics of acetoacetamide and potassium sulfite ant pH 8 and 21° C.

As can be seen, from FIG. 1, at 15 minutes, Potassium Sulphite scavenger has reached substantially 100% reaction (+/−5% error) completion whereas Acetoacetamide has achieved only approximately 35% reaction completion.

Optional Composition Ingredients

The liquid compositions of the present invention may comprise other ingredients selected from the list of optional ingredients set out below. Unless specified herein below, an "effective amount" of a particular laundry adjunct is preferably from 0.01%, more preferably from 0.1%, even more preferably from 1% to 20%, more preferably to 15%, even more preferably to 10%, still even more preferably to 7%, most preferably to 5% by weight of the detergent compositions.

Pearlescent Agent

In one embodiment of the present invention the composition may comprise a pearlescent agent.

The pearlescent agents may be organic or inorganic. Typical examples of organic pearlescent agents include monoesters and/or diesters of ethylene glycol, propylene glycol, diethylene glycol, dipropylene glycol, triethylene glycol or tetraethylene glycol with fatty acids containing from about 6 to about 22, preferably from about 12 to about 18 carbon atoms, such as caproic acid, caprylic acid, 2-ethyhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid, erucic acid, and mixtures thereof.

Preferred inorganic pearlescent Agents include those selected from the group consisting of mica, metal oxide coated mica, silica coated mica, bismuth oxychloride coated mica, bismuth oxychloride, myristyl myristate, glass, metal oxide coated glass, guanine, glitter (polyester or metallic) and mixtures thereof. Suitable micas includes muscovite or potassium aluminum hydroxide fluoride. The platelets of mica are preferably coated with a thin layer of metal oxide. Preferred metal oxides are selected from the group consisting of rutile, titanium dioxide, ferric oxide, tin oxide, alumina and mixtures thereof. The crystalline pearlescent layer is formed by calcining mica coated with a metal oxide at about 732° C. The heat creates an inert pigment that is insoluble in resins, has a stable color, and withstands the thermal stress of subsequent processing Surfactants or Detersive Surfactants The compositions of the present invention may comprise from about 1% to 80% by weight of a surfactant. Preferably such compositions comprise from about 5% to 50% by weight of surfactant.

Detersive surfactants utilized can be of the anionic, nonionic, zwitterionic, ampholytic or cationic type or can comprise compatible mixtures of these types. More preferably surfactants are selected from the group consisting of anionic, nonionic, cationic surfactants and mixtures thereof. Preferably the compositions are substantially free of betaine surfactants. Detergent surfactants useful herein are described in U.S. Pat. No. 3,664,961, Norris, issued May 23, 1972, U.S. Pat. No. 3,919,678, Laughlin et al., issued Dec. 30, 1975, U.S. Pat. No. 4,222,905, Cockrell, issued Sep. 16, 1980, and in U.S. Pat. No. 4,239,659, Murphy, issued Dec. 16, 1980. Anionic and nonionic surfactants are preferred.

Useful anionic surfactants can themselves be of several different types. For example, water-soluble salts of the higher fatty acids, i.e., “soaps”, are useful anionic surfactants in the compositions herein. This includes alkali metal soaps such as the sodium, potassium, ammonium, and alkyl ammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap. Soaps also have a useful building function.

Additional non-soap anionic surfactants which are suitable for use herein include the water-soluble salts, preferably the alkali metal, and ammonium salts, of organic sulfuric reaction products having in their molecular structure an alkyl group containing from about 10 to about 20 carbon atoms, a sulfonic acid or sulfuric acid ester group and optional alkoxylation. (Included in the term “alkyl” is the alkyl portion of acyl groups.) Examples of this group of synthetic surfactants are a) the sodium, potassium and ammonium alkyl sulfates, especially those obtained by sulfating the higher alcohols ($C_8$-$C_{18}$ carbon atoms) such as those produced by reducing the glycerides of tallow or coconut oil; b) the sodium, potassium and ammonium alkyl polyethoxylate sulfates, particularly those in which the alkyl group contains from 10 to 22, preferably from 12 to 18 carbon atoms, and wherein the polyethoxylate chain contains from 1 to 15, preferably 1 to 6 ethoxylate moieties; and c) the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11}$-$C_{13}$ LAS.

Preferred nonionic surfactants are those of the formula $R^1(OC_2H_4)_nOH$, wherein $R^1$ is a $C_{10}$-$C_{16}$ alkyl group or a $C_8$-$C_{12}$ alkyl phenyl group, and n is from 3 to about 80. Particularly preferred are condensation products of $C_{12}$-$C_{15}$ alcohols with from about 5 to about 20 moles of ethylene oxide per mole of alcohol, e.g., $C_{12}$-$C_{13}$ alcohol condensed with about 6.5 moles of ethylene oxide per mole of alcohol.

Fabric Care Benefit Agents

The compositions of the present invention may comprise a fabric care benefit agent. As used herein, “fabric care benefit agent” refers to any material that can provide fabric care benefits such as fabric softening, color protection, pill/fuzz reduction, anti-abrasion, anti-wrinkle, and the like to garments and fabrics, particularly on cotton and cotton-rich garments and fabrics, when an adequate amount of the material is present on the garment/fabric. Non-limiting examples of fabric care benefit agents include cationic surfactants, silicones, polyolefin waxes, latexes, oily sugar derivatives, cationic polysaccharides, polyurethanes, fatty acids and mixtures thereof. Fabric care benefit agents when present in the composition, are suitably at levels of up to about 30% by weight of the composition, more typically from about 1% to about 20%, preferably from about 2% to about 10% in certain embodiments.

Preferred fabric care benefit agents include silicone fluids such as poly(di)alkyl siloxanes, especially polydimethyl siloxanes and cyclic silicones.

Detersive Enzymes

Suitable detersive enzymes for optional use herein include protease, amylase, lipase, cellulase, carbohydrase including mannanase and endoglucanase, and mixtures thereof. Enzymes can be used at their art-taught levels, for example at levels recommended by suppliers such as Novo and Genencor. Typical levels in the compositions are from about 0.0001% to about 5%. When enzymes are present, they can be used at very low levels, e.g., from about 0.001% or lower, in certain embodiments of the invention; or they can be used in heavier-duty laundry detergent formulations in accordance with the invention at higher levels, e.g., about 0.1% and higher. In accordance with a preference of some consumers for “non-biological” detergents, the present invention includes both enzyme-containing and enzyme-free embodiments.

Deposition Aid

As used herein, “deposition aid” refers to any cationic or amphoteric polymer or combination of cationic and amphoteric polymers that significantly enhance the deposition of the fabric care benefit agent onto the fabric during laundering. Preferably, the deposition aid, where present, is a cationic or amphoteric polymer. The amphoteric polymers of the present invention will also have a net zero or cationic charge, i.e.; the total cationic charges on these polymers will equal or exceed the total anionic charge. The charge density of the polymer ranges from about 0.0 milliequivalents/g to about 6 milliequivalents/g. The charge density is calculated by dividing the number of net charge per repeating unit by the molecular weight of the repeating unit. In one embodiment, the charge density varies from about 0.0 milliequivants/g to about 3 milliequivalents/g. The positive charges could be on the backbone of the polymers or the side chains of polymers.

Rheology Modifier

In a preferred embodiment of the present invention, the composition comprises a rheology modifier. The rheology modifier is selected from the group consisting of non-polymeric crystalline, hydroxy-functional materials, polymeric rheology modifiers which impart shear thinning characteristics to the aqueous liquid matrix of the composition.

Generally the rheology modifier will comprise from 0.01% to 1% by weight, preferably from 0.05% to 0.75% by weight, more preferably from 0.1% to 0.5% by weight, of the compositions herein.

Structuring agent which are especially useful in the compositions of the present invention comprises non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. Preferred rheology modifiers include crystalline, hydroxyl-containing rheology modifiers include castor oil and its derivatives. Especially preferred are hydrogenated castor oil derivatives such as hydrogenated castor oil and hydrogenated castor wax. A preferred rheology modifier is castor oil-based, crystalline, hydroxyl-containing rheology modifier commercially available under the tradename THIXCIN® from Rheox, Inc. (now Elementis).

Other types of rheology modifiers, besides the non-polymeric, crystalline, hydroxyl-containing rheology modifiers described hereinbefore, may be utilized in the liquid detergent compositions herein. Polymeric materials which will provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

In the absence of rheology modifier and in order to impart preferred shear thinning characteristics to the liquid composition, the liquid composition can be internally structured through surfactant phase chemistry or gel phases.

Builder

The compositions of the present invention may optionally comprise a builder. Suitable builders are discussed below:

Suitable polycarboxylate builders include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Oxydisuccinates are also especially useful in such compositions and combinations.

Specific examples of nitrogen-containing, phosphor-free aminocarboxylates include ethylene diamine disuccinic acid and salts thereof (ethylene diamine disuccinates, EDDS), ethylene diamine tetraacetic acid and salts thereof (ethylene diamine tetraacetates, EDTA), and diethylene triamine penta acetic acid and salts thereof (diethylene triamine penta acetates, DTPA).

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Bleach System

Bleach system suitable for use herein contains one or more bleaching agents. Nonlimiting examples of suitable bleaching agents are selected from the group consisting of catalytic metal complexes, activated peroxygen sources, bleach activators, bleach boosters, photobleaches, bleaching enzymes, free radical initiators, and hyohalite bleaches.

Suitable activated peroxygen sources include, but are not limited to, preformed peracids, a hydrogen peroxide source in combination with a bleach activator, or a mixture thereof. Suitable preformed peracids include, but are not limited to, compounds selected from the group consisting of percarboxylic acids and salts, percarbonic acids and salts, perimidic acids and salts, peroxymonosulfuric acids and salts, and mixtures thereof. Suitable sources of hydrogen peroxide include, but are not limited to, compounds selected from the group consisting of perborate compounds, percarbonate compounds, perphosphate compounds and mixtures thereof. Suitable types and levels of activated peroxygen sources are found in U.S. Pat. Nos. 5,576,282, 6,306,812 and 6,326,348.

Perfume

Perfumes are preferably incorporated into the detergent compositions of the present invention. The perfume ingredients may be premixed to form a perfume accord prior to adding to the detergent compositions of the present invention. As used herein, the term "perfume" encompasses individual perfume ingredients as well as perfume accords. More preferably the compositions of the present invention comprise perfume microcapsules.

The level of perfume accord in the detergent composition is typically from about 0.0001% to about 5% or higher, e.g., to about 10%; preferably from about 0.0002% to about 4.0%, more preferably from about 0.003% to about 3.0. %, most preferably from about 0.005% to about 2.0% by weight of the detergent composition.

Solvent System

The solvent system in the present compositions can be a solvent system containing water alone or mixtures of organic solvents with water. Preferred organic solvents include 1,2-propanediol, ethanol, glycerol, dipropylene glycol, methyl propane diol and mixtures thereof. Other lower alcohols, $C_1$-$C_4$ alkanolamines such as monoethanolamine and triethanolamine, can also be used. Solvent systems can be absent, for example from anhydrous solid embodiments of the invention, but more typically are present at levels in the range of from about 0.1% to about 98%, preferably at least about 10% to about 95%, more usually from about 25% to about 75%.

Fabric substantive and Hueing Dye

Dyes are conventionally defined as being acid, basic, reactive, disperse, direct, vat, sulphur or solvent dyes, etc. For the purposes of the present invention, direct dyes, acid dyes and reactive dyes are preferred, direct dyes are most preferred. Direct dye is a group of water-soluble dye taken up directly by fibers from an aqueous solution containing an electrolyte, presumably due to selective adsorption. In the Color Index system, directive dye refers to various planar, highly conjugated molecular structures that contain one or more anionic sulfonate group. Acid dye is a group of water soluble anionic dyes that is applied from an acidic solution. Reactive dye is a group of dyes containing reactive groups capable of forming covalent linkages with certain portions of the molecules of natural or synthetic fibers. From the chemical structure point of view, suitable fabric substantive dyes useful herein may be an azo compound, stilbenes, oxazines and phthalocyanines.

Suitable fabric substantive dyes for use herein include those listed in the Color Index as Direct Violet dyes, Direct Blue dyes, Acid Violet dyes and Acid Blue dyes.

The hueing dye is included in the laundry detergent composition in an amount sufficient to provide a tinting effect to fabric washed in a solution containing the detergent. In one embodiment, the composition comprises, by weight, from about 0.0001% to about 0.05%, more specifically from about 0.001% to about 0.01%, of the hueing dye.

Exemplary hueing dyes include triarylmethane blue and violet basic dyes as set forth in Table 2, methine blue and violet basic dyes as set forth in Table 3, anthraquinone dyes as set forth in Table 4, anthraquinone dyes basic blue 35 and basic blue 80, azo dyes basic blue 16, basic blue 65, basic blue 66 basic blue 67, basic blue 71, basic blue 159, basic violet 19, basic violet 35, basic violet 38, basic violet 48, oxazine dyes basic blue 3, basic blue 75, basic blue 95, basic blue 122, basic blue 124, basic blue 141, Nile blue A and xanthene dye basic violet 10, and mixtures thereof.

Encapsulated Composition

The compositions of the present invention may be encapsulated within a water-soluble film. The water-soluble film may be made from polyvinyl alcohol or other suitable variations, carboxy methyl cellulose, cellulose derivatives, starch, modified starch, sugars, PEG, waxes, or combinations thereof.

In another embodiment the water-soluble film may include a co-polymer of vinyl alcohol and a carboxylic acid. U.S. Pat. No. 7,022,656 B2 (Monosol) describes such film compositions and their advantages. One benefit of these copolymers is the improvement of the shelf-life of the pouched detergents thanks to the better compatibility with the detergents. Another advantage of such films is their better cold water (less than 10° C.) solubility. Where present the level of the co-polymer in the film material, is at least 60% by weight of the film. The polymer can have any weight average molecular weight, preferably from 1000 daltons to 1,000,000 daltons, more preferably from 10,000 daltons to 300,000 daltons, even more preferably from 15,000 daltons to 200,000 daltons, most preferably from 20,000 daltons to 150,000 daltons. Preferably, the co-polymer present in the film is from 60% to 98% hydrolysed, more preferably 80% to 95% hydrolysed, to improve the dissolution of the material. In a highly preferred execution, the co-polymer comprises from 0.1 mol % to 30 mol %, preferably from 1 mol % to 6 mol %, of said carboxylic acid.

The water-soluble film of the present invention may further comprise additional co-monomers. Suitable additional co-monomers include sulphonates and ethoxylates. An example of preferred sulphonic acid is 2-acrylamido-2-methyl-1-propane sulphonic acid (AMPS). A suitable water-soluble film for use in the context of the present invention is commercially available under tradename M8630™ from Mono-Sol of Indiana, US. The water-soluble film herein may also comprise ingredients other than the polymer or polymer material. For example, it may be beneficial to add plasticisers, for example glycerol, ethylene glycol, diethyleneglycol, propane diol, 2-methyl-1,3-propane diol, sorbitol and mixtures thereof, additional water, disintegrating aids, fillers, anti-foaming agents, emulsifying/dispersing agents, and/or antiblocking agents. It may be useful that the pouch or water-soluble film itself comprises a detergent additive to be delivered to the wash water, for example organic polymeric soil release agents, dispersants, dye transfer inhibitors. Optionally the surface of the film of the pouch may be dusted with fine powder to reduce the coefficient of friction. Sodium aluminosilicate, silica, talc and amylose are examples of suitable fine powders.

The encapsulated pouches of the present invention can be made using any convention known techniques. More preferably the pouches are made using horizontal form filling thermoforming techniques.

Other Adjuncts

Examples of other suitable cleaning adjunct materials include, but are not limited to, alkoxylated benzoic acids or salts thereof such as trimethoxy benzoic acid or a salt thereof (TMBA); enzyme stabilizing systems; chelants including aminocarboxylates, aminophosphonates, nitrogen-free phosphonates, and phosphorous- and carboxylate-free chelants; inorganic builders including inorganic builders such as zeolites and water-soluble organic builders such as polyacrylates, acrylate/maleate copolymers and the likescavenging agents including fixing agents for anionic dyes, complexing agents for anionic surfactants, and mixtures thereof; effervescent systems comprising hydrogen peroxide and catalase; optical brighteners or fluorescers; soil release polymers; dispersants; suds suppressors; dyes; colorants; filler salts such as sodium sulfate; hydrotropes such as toluenesulfonates, cumenesulfonates and naphthalenesulfonates; photoactivators; hydrolysable surfactants; preservatives; anti-oxidants; anti-shrinkage agents; anti-wrinkle agents; germicides; fungicides; color speckles; colored beads, spheres or extrudates; sunscreens; fluorinated compounds; clays; luminescent agents or chemiluminescent agents; anti-corrosion and/or appliance protectant agents; alkalinity sources or other pH adjusting agents; solubilizing agents; processing aids; pigments; free radical scavengers, and mixtures thereof. Suitable materials include those described in U.S. Pat. Nos. 5,705,464, 5,710,115, 5,698,504, 5,695,679, 5,686,014 and 5,646,101. Mixtures of adjuncts—Mixtures of the above components can be made in any proportion.

Composition Preparation

The compositions herein can generally be prepared by first preparing a slurry of microcapsules and optionally a formaldehyde scavenger, preferably a non-sulfur containing formaldehyde scavenger, and then combining said slurry with the remaining ingredients including the sulfur-containing formaldehyde scavenger.

If a rheology modifier is used, it is preferred to first form a pre-mix within which the rheology modifier is dispersed in a portion of the water eventually used to comprise the compositions and then combine the premix with the composition.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Examples 1 and 2 are examples of preferred microcapsules and methods for making same.

Example 1

84 wt % Core/16 wt % Wall Melamine Formaldehyde (MF) Capsule 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um was obtained as analyzed by a Model 780 Accusizer.

Example 2

80 wt % Core/20 wt % Wall Melamine Formaldehyde Capsule 18 grams of a blend of 50% butyl acrylate-acrylic acid copolymer emulsifier (Colloid C351, 25% solids, pka 4.5-

4.7, Kemira) and 50% polyacrylic acid (35% solids, pKa 1.5-2.5, Aldrich) is dissolved and mixed in 200 grams deionized water. The pH of the solution is adjusted to pH of 3.5 with sodium hydroxide solution. 6.5 grams of partially methylated methylol melamine resin (Cymel 385, 80% solids Cytec) is added to the emulsifier solution. 200 grams of perfume oil is added to the previous mixture under mechanical agitation and the temperature is raised to 60° C. After mixing at higher speed until a stable emulsion is obtained, the second solution and 3.5 grams of sodium sulfate salt are poured into the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.6, 30 grams of partially methylated methylol melamine resin (Cymel 385, 80% Cytec). This mixture is heated to 75° C. and maintained 6 hours with continuous stirring to complete the encapsulation process. 23 grams of acetoacetamide (Sigma-Aldrich, Saint Louis, Mo., U.S.A.) is added to the suspension. To demonstrate the benefit of the present invention, the Applicants prepared liquid detergent matrix A, in table 1 below.

TABLE 1

| Active Material in weight % | A |
|---|---|
| C14-C15 alkyl poly ethoxylate 7 | 3.39 |
| C12-C14 alkyl poly ethoxylate 7 | 1.13 |
| C12-C14 alkyl poly ethoxylate 3 sulfate Na salt | 7.66 |
| Alkylbenzene sulfonic acid | 1.17 |
| Citric Acid | 2.73 |
| C12-18 fatty acid | 5.06 |
| Enzymes | 0.2 |
| Boric Acid | 1.40 |
| Trans-sulphated ethoxylated hexamethylene diamine quat | 0.81 |
| Diethylene triamine penta methylene phosphonic acid | 0.12 |
| Hydrogenated Castor Oil structurant | 0.300 |
| Ethanol | 1.59 |
| 1,2 propanediol | 0.07 |
| Sodium hydroxide | 3.48 |

TABLE 1-continued

| Active Material in weight % | A |
|---|---|
| Silicone PDMS emulsion | 0.0025 |
| Blue Dye | 0.0006 |
| Preservative Acticide MBS 2550 (ex Thor) | 0.0135 |
| Perfume | Nil |
| Merquat 5300 polymer (1) | 0.19 |
| Water | Up to 95% |

From this liquid detergent A, a number of samples (A1-A9) were made through addition of different levels of scavengers, micro capsules, perfume and water (up to 100). The blue detergent samples were placed in storage for 4 months at 35° C. in glass bottles, and protected with aluminum foil from the day light. After storage, the product discoloration of the detergent samples is graded by two different trained color graders, utilizing a PSU scale. The PSU scale as referenced herein is a paired comparison between the color of reference liquid laundry detergent A1 and the color of test liquid laundry detergent A2 to A9. The glass bottles with detergent are compared next to each other in standard day light conditions. The distance between the grader and the samples is 2 meters, and the samples are at eye height. The grading scale is from 0 to 4 (see below in Table 2). The grading for each laundry detergent is the average of the grades given by the 2 trained color graders. Results are provided in Table 3.

TABLE 2

| PSU Grading Scale | |
|---|---|
| SCORE | MEANING |
| 0 | There is no difference |
| 1 | I think this one is more greenish (unsure) |
| 2 | I know this one is more greenish (sure) |
| 3 | This one is a lot more greenish |
| 4 | This one is clearly green |

TABLE 3

| | A1 | A2 | A3 | A4 | A5 | A6 | A7 | A8 | A9 |
|---|---|---|---|---|---|---|---|---|---|
| Scavenger 1 Acetoacetamide | — | — | 0.035% | 0.035% | 0.035% | 0.035% | 0.035% | 0.035% | 0.035% |
| Scavenger 2 K-sulphite | — | — | — | — | — | — | 0.1 | 0.2 | 0.2 |
| PMC (2) | — | 0.3 | 0.3 | 0.3 | — | — | 0.3 | 0.3 | — |
| PaMC (3) | — | — | — | — | 0.3 | 0.3 | — | — | 0.3 |
| Perfume | — | — | — | 0.6 | — | 0.6 | 0.6 | 0.6 | — |
| Water | Up to | Up to | Up to 100 | Up to 100 | Up to 100 | Up to 100 | Up to 100 | Up to 100 | Up to 100 |
| Detergent discoloration after 4 months storage at 35° C. (PSU) | Ref | 4 | 4 | 4 | 4 | 4 | 1.5 | 0.5 | 0.5 |
| PASS if Delta PSU < 2 | Ref | FAIL | FAIL | FAIL | FAIL | FAIL | PASS | PASS | PASS |

(1) Merquat 5300: terpolymer with mole ratio: 90% PAM/5% AA/5% MAPTAC produced by Nalco.

(2) PMC: Perfume Micro Capsule: Perfume oil encapsulated in a melamine-formaldehyde shell (3) PaMC: Paraffin Micro Capsule: Paraffin oil (Marcol 152 ex Exxon) encapsulated in melamine-formaldehyde shell Levels for (2) and (3) are expressed as perfume oil or paraffin oil delivered via capsules.

The following are examples of liquid compositions according to the present invention that pass the above success criteria, table 4.

TABLE 4

| Active Material in weight % Composition pH: 7.5-8.5 | 1 | 2 | 3 | 4 | 5 | 6 |
|---|---|---|---|---|---|---|
| C14-C15 alkyl poly ethoxylate 7 | 6.0 | 6.0 | 6.0 | 6.0 | 3.39 | 6.0 |
| C12-C14 alkyl poly ethoxylate 7 | 2.0 | 2.0 | 2.0 | 2.0 | 1.13 | 2.0 |
| C12-C14 alkyl poly ethoxylate 3 sulfate Na salt | 13.55 | 13.55 | 13.55 | 13.55 | 7.66 | 13.55 |
| Alkylbenzene sulfonic acid | 1.17 | 1.17 | 1.17 | 1.17 | 1.17 | 1.17 |
| Citric Acid | 4.83 | 4.83 | 4.83 | 4.83 | 2.73 | 4.83 |
| C12-18 fatty acid | 8.95 | 8.95 | 8.95 | 8.95 | 5.06 | 8.95 |
| Enzymes | 0.8 | 0.8 | 0.8 | 0.8 | 0.2 | 0.4 |
| Boric Acid | 1.92 | 1.92 | 1.92 | 1.92 | 1.40 | 1.92 |
| Trans-sulphated ethoxylated hexamethylene diamine quat | 1.43 | 1.43 | 1.43 | 1.43 | 0.81 | 1.43 |
| Diethylene triamine penta methylene phosphonic acid | 0.21 | 0.21 | 0.21 | 0.21 | 0.12 | 0.21 |
| Hydrogenated Castor Oil structurant | 0.3 | 0.3 | 0.3 | 0.3 | 0.3 | 0.3 |
| Ethanol | 2.2 | 2.2 | 2.2 | 2.2 | 1.59 | 2.2 |
| 1,2 propanediol | 0.27 | 0.27 | 0.27 | 0.27 | 0.07 | 0.27 |
| Glycerol | — | — | — | — | 0.05 | 0.05 |
| Sodium hydroxide | 6.2 | 6.2 | 6.2 | 6.2 | 3.48 | 6.2 |
| Silicone PDMS emulsion | 0.0025 | 0.0025 | 0.0025 | 0.0025 | 0.0025 | 0.0025 |
| Dye | 0.0006 | 0.0006 | 0.0006 | 0.0006 | 0.0008 | 0.0006 |
| Preservative Acticide MBS2550 | — | — | — | — | 0.0135 | — |
| Mearlin Superfine 9120V+ pearl agent (ex BASF) | — | — | — | — | 0.05 | 0.05 |
| Perfume | — | — | 0.6 | 0.6 | 0.65 | 1.3 |
| Merquat 5300(1) | 0.3 | 0.3 | 0.3 | 0.3 | 0.19 | 0.3 |
| Acetoacetamide | 0.07 | 0.075 | — | — | 0.035 | 0.07 |
| $NH_4OH$ | — | — | 0.05 | — | — | — |
| PMC: Perfume microcapsules(2) | 0.6 | — | 0.6 | 0.6 | 0.3 | 0.6 |
| PaMC: Paraffin microcapsule(3) | — | 0.65 | — | — | — | — |
| Potassium Sulphite | 0.2 | 0.3 | 0.4 | 0.4 | 0.1 | 0.2 |
| Water | Up to 100 | Up to 100 | Up to 100 | Up to 100 | Up to 100 | Up to 100 |

(1)Merquat 5300: terpolymer with mole ratio: 90% PAM/5% AA/5% MAPTAC produced by Nalco.
(2)PMC: Perfume Micro Capsule: Perfume oil encapsulated in a melamine-formaldehyde shell
(3)PaMC: Paraffin Micro Capsule: Paraffin oil (Marcol 152 ex Exxon) encapsulated in melamine-formaldehyde shell
Levels for (2) and (3) are expressed as perfume oil or paraffin oil delivered via capsules.

The following are examples of unit dose executions wherein the liquid composition is enclosed within a PVA film (Table 5). The preferred film used in the present examples is Monosol M8630 76 μm thickness.

TABLE 5

| Active Material in weight % Composition pH 7.5 for a pouch (39 mL) | 16 | 17 | 18 | 19 | 20 |
|---|---|---|---|---|---|
| Alkylbenzene sulfonic acid | 22.60 | 22.60 | 22.60 | 22.60 | 22.60 |
| C12-14 Alcohol ethoxylate EO7 | 16.49 | 16.49 | 16.49 | 16.49 | 16.49 |
| C12-18 fatty acid | 17.70 | 17.70 | 17.70 | 17.70 | 17.70 |
| Protease | 0.3 | 0.3 | 0.3 | 0.3 | 0.3 |
| Silicone oil (PDMS) | 1.23 | 1.23 | 1.23 | 1.23 | 1.23 |
| Optical brightener | 0.27 | 0.27 | 0.27 | 0.27 | 0.27 |
| Propylene glycol | 13.14 | 13.14 | 13.14 | 13.14 | 13.14 |
| Glycerol | 6.89 | 6.89 | 6.89 | 6.89 | 6.89 |
| Monoethanolamine | 6.74 | 6.74 | 6.74 | 6.74 | 6.74 |
| Caustic soda | 1.09 | 1.09 | 1.09 | 1.09 | 1.09 |
| Potassium sulfite | 0.17 | 0.30 | 0.30 | 0.30 | 0.30 |
| Added water | 1.97 | 1.97 | 1.97 | 1.97 | 1.97 |
| Hydrogenated castor oil | 0.23 | 0.23 | 0.23 | 0.23 | 0.23 |
| PMC: Perfume microcapsule (2) | 0.45 | 1.00 | 1.0 | 1.0 | 1.0 |
| Acetoacetamide | 0.05 | 0.11 | 0.11 | — | — |
| NH4OH | — | — | — | 0.1 | 0.1 |
| Perfume | 1.89 | 1.89 | 1.89 | 1.89 | 1.89 |
| Dyes | 0.0058 | 0.0058 | 0.0058 | 0.0058 | 0.0058 |
| Mearlin MP3001 pearl agent (ex BASF) | | | 0.10 | | |
| Water | To 100 | To 100 | To 100 | To 100 | To 100 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid composition encapsulated within a water-soluble film comprising a microcapsule, said microcapsule comprising an aldehyde-containing resin, from about 0.001% to about 2.0%, by weight of said composition of one or more sulfur-based formaldehyde scavenger, wherein the one or more sulfur-based formaldehyde scavenger is selected from the group consisting of alkali metal pyrosulfites, sulfites, bisulfite, and mixtures thereof, and from about 0.0001% to about 1%, by weight of said composition of a non-sulfur-based formaldehyde scavenger, wherein the non-sulfur-based formaldehyde scavenger is acetoacetamide, wherein said microcapsule comprises a microcapsule wall material having a ratio, by weight, of said one or more sulfur-based formaldehyde scavenger to said microcapsule wall material of from about 0.05:1 to about 10:1; said formaldehyde scavengers react with formaldehyde to achieve more than about 60% reaction completeness in about 15 minutes time at pH 8 and at about 21° C.; said composition, after four months storage at 35° C., has a detergent discoloration score, Panel Score Unit (PSU), of less than 2; and said composition comprises anionic surfactant.

2. The composition according to claim 1, wherein the microcapsule is a core in shell microcapsule comprising a substance selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof.

3. The composition according to claim 1, wherein the liquid composition further comprises a compound selected from the group consisting of alkali or alkali earth metal dithionites, sulfides, thiosulfates and thiocyanates, mercaptans, such as thioglycolic acid, mercaptoethanol, 4-hydroxy-2-mercapto-6-methylpyrimidine, mercaptothiazoline, thiodialkanoic acids, such as thiodipropionic acid, dithiodialkanoic acids, such as 3,3'-dithiodipropionic acid, sulfinates, such as sodium formaldehydesulfoxylate or formamidinosulfinic acid and thiourea and mixtures thereof.

4. The composition according to claim 1, wherein the liquid composition further comprises another non-sulfur-based formaldehyde scavenger is selected from the group consisting of urea, ethylene urea, lysine, glycine, serine, carnosine, histidine, 3,4-diaminobenzoic acid, allantoin, glycouril, anthranilic acid, methyl anthranilate, methyl 4-aminobenzoate, ethyl acetoacetate, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanolamine, succinamide, benzotriazole, triazole, indoline, oxamide, sorbitol, glucose, cellulose, poly (vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexanediol, ethylenediamine-N,N'-bisacetoacetamide, N-(2-ethylhexyl) acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexanecarboxaldehyde, 2,2-dimethyl-1,3-dioxan-4,6-dione, 2-pentanone, dibutyl amine, triethylenetetramine, benzylamine, hydroxycitronellol, cyclohexanone, 2-butanone, pentanedione, dehydroacetic acid, ammonium hydroxide, and mixtures thereof.

5. The liquid composition according to claim 1, wherein said composition comprises a pre-made slurry which comprises said microcapsule and said non-sulfur based formaldehyde scavenger.

6. The liquid composition according to claim 1, wherein said one or more sulfur-based formaldehyde scavenger is selected from the group consisting of alkali metal sulfite, bisulfite, and mixtures thereof.

7. A liquid composition encapsulated within a water-soluble film comprising a microcapsule, said microcapsule comprising an aldehyde-containing resin, from about 0.001% to about 2.0% by weight of said composition of one or more sulfur-based formaldehyde scavenger selected from the group consisting of alkali metal sulfite, bisulfite, pyrosulfite, and mixtures thereof, from about 0.0001% to about 1% by weight of said composition of a non-sulfur-based formaldehyde scavenger comprising acetoacetamide, and anionic surfactant, wherein said formaldehyde scavengers react with formaldehyde to achieve more than about 60% reaction completeness in about 15 minutes time at pH 8 and at about 21° C., said composition, after four months storage at 35° C., has a detergent discoloration score, Panel Score Unit (PSU) of less than 2.

* * * * *